United States Patent [19]

Heinsohn et al.

[11] Patent Number: 4,620,030

[45] Date of Patent: Oct. 28, 1986

[54] PREPARATION OF METHYL ISOCYANATE IN A QUARTZ REACTOR

[75] Inventors: George E. Heinsohn, Elkton, Md.; Velliyur N. M. Rao, Wilmington, Del.

[73] Assignee: E. I. Du Pont de Nemours and Company, Wilmington, Del.

[21] Appl. No.: 663,847

[22] Filed: Oct. 23, 1984

[51] Int. Cl.[4] ............................................. C07C 71/00
[52] U.S. Cl. .................................................... 560/338
[58] Field of Search ..................... 260/453 P; 560/338

[56] References Cited

U.S. PATENT DOCUMENTS 4,469,640 9/1984 Carcia et al. .................... 260/453 P Primary Examiner—Alan Siegel

[57] ABSTRACT

The process in which methyl isocyanate is prepared by the oxidative dehydrogenation of monomethyl formamide is improved by performing the reaction in a quartz reactor.

1 Claim, No Drawings

PREPARATION OF METHYL ISOCYANATE IN A QUARTZ REACTOR

BACKGROUND OF THE INVENTION

U.S. Pat. No. 4,207,251 discloses the catalyzed gas phase production of $C_1$–$C_{24}$ organo-isocyanates by oxidative dehydrogenation of the corresponding N-monosubstituted formamides. The reactors disclosed are of stainless-steel construction. Although satisfactory yields of the higher isocyanates can be obtained according to the process of the above patent using stainless-steel reactors, poorer yields are obtained when preparing methyl isocyanate.

SUMMARY OF THE INVENTION

The present invention provides an improved process for the preparation of methyl isocyanate by the gas-phase reaction of monomethyl formamide with oxygen at 400°–700° C. in the presence of a silver-containing catalyst, wherein the improvement comprises carrying out the reaction in a quartz reactor.

DETAILED DESCRIPTION OF THE INVENTION

The present invention provides an improved manner of conducting the process for the preparation of isocyanates disclosed in U.S. Pat. No. 4,207,251. That process involves the gas phase oxidative dehydrogenation of an N-monosubstituted formamide of the formula $R(NHCHO)_n$, where R is a substituted or unsubstituted alkyl, cycloalkyl, aryl, alkaryl, or aralkyl group and n is 1 or 2, to the corresponding isocyanate of the formula $R-(NCO)_n$. The oxidizing agent is oxygen, supplied to the reaction either pure or as part of an oxygen-containing gas, such as air. The reaction is performed at 300°–600° C. in the presence of a catalyst of copper and/or one or more metals of the groups IB and VIII of the 5th and 6th periods of the groups IB and VIII of the 5th and 6th periods of the Periodic Table of Elements. Details of the reaction, including reactants and process conditions, are provided in U.S. Pat. No. 4,207,251 and the disclosures of that patent are incorporated herein by reference as the context in which the present invention operates.

It has been found, however, that the higher isocyanates can be obtained in satisfactory yields according to the above process, but that the yield of methyl isocyanate obtained under the process conditions of U.S. Pat. No. 4,207,251 is comparatively poor. As part of the present invention, it has been found the stainless-steel and other metals and metal-alloys, the materials of construction disclosed for the reactors in the patent, can catalyze the decomposition of methyl isocyanate and monomethyl formamide under the disclosed process conditions. According to the present invention decomposition can be substantially minimized and higher yields of methyl isocyanate obtained by using a quartz reactor.

The catalysts preferred for use in the present invention contain silver and are either pure silver or a combination of silver and one of the other metals described as a catalyst for the oxidative dehydrogenation. Gold is preferred for use when the catalyst is to contain silver in combination with another metal.

It is preferred to use a catalyst in the form of crystals or sputtered (vapor deposited) or ion plated on an inert support. When either of the latter two forms is used, generally the silver or silver/metal combination will comprise from 0.05–50 weight percent of the total catalyst composition. Generally the catalyst support will be a hard, nonporous refractory particulate material, preferably ceramic, having a mean particle diameter in the range of from 0.1 micron to 0.5 centimeter. The support should have a surface area below about 20 square meters per gram and preferably less than 3 square meters per gram. Alumina and silica are the preferrd catalyst supports, although other oxides such as ceria, yttria, zirconia, or titania can be used. These catalysts, and their method of preparation, are disclosed in U.S. Pat. No. 4,469,640 incorporated herein by reference.

Generally, the process of the present invention is carried out at 400°–650° C. A temperature of up to 700° C. can be used, but normally temperatures higher than this should be avoided. A reaction temperature of about 450°–625° C. is preferred.

The absolute pressure of the gas phase reaction mixture is not critical and can be varied from about 100 to 1000 kPA. It is preferred that the reaction be carried out at an absolute pressure of about one atmosphere (100 kPA).

Methyl isocyanate is used in the production of certain insecticides including S-methyl-N-[(methylcarbamoyl)oxy]thioacetimidate (methomyl).

EXAMPLES 1–3

The procedure in each of the examples was as follows. Silver crystals were packed in a metal cylinder to form a catalyst bed with a depth of 2.5 cm. The cylinder in each case was 4 cm in length, 0.1 mm in wall thickness, and of a material of construction as shown in the Table. The cylinder, designed to function as a reactor containing the catalyst bed, was tightly fitted into a vertically positioned quartz tube (18 cm in length; 10 mm inside diameter). An electric heating element was positioned around the quartz tube to provide uniform heat to the cylinder inside, and the catalyst bed was brought to a temperature of 495° C. Monomethyl formamide was evaporated at a rate of about 0.29 g per minute and mixed at atmospheric pressure with 134 cc per minute of air (0.51 equivalent of oxygen) and 514 cc per minute pure nitrogen. The gas stream mixture was heated to 250° C. and passed through the catalyst bed. The effluent was passed into a standard laboratory glass tube condenser (15 cm in length; 12 mm inside diameter) jacketed with water chilled to 0° C. in order to remove unreacted monomethyl formamide and other high boiling components. The remaining gas phase mixture and the condensate were each analyzed by gas chromatography to determine the amount of monomethyl formamide that had been converted and the yield of methyl isocyanate (moles of methyl isocyanate recovered per mole of monomethyl formamide converted, expressed as percentage).

EXAMPLE 4

The example was conducted exactly as described for Examples 1–3 except that no metal cylinder was used; the silver catalyst was packed directly inside the quartz tube, which functioned as the reactor.

Table of Results

| Example | Material of Construction of Reactor | Methyl Isocyanate Yield (%) |
| --- | --- | --- |
| 1 | Stainless Steel (#304) | 45 |
| 2 | Copper | 67 |
| 3 | Nickel | 38 |
| 4 | Quartz | 71 |

What is claimed is:

1. In a process for the preparation of methyl isocyanate by the gas-phase reaction of monomethyl formamide with oxygen at 400°–700° C. in the presence of a silver-containing catalyst, the improvement comprising carrying out the reaction in a quartz reactor.